US010178217B2

(12) United States Patent
Corbin et al.

(10) Patent No.: US 10,178,217 B2
(45) Date of Patent: Jan. 8, 2019

(54) TELECARE-ENABLED MOBILE TERMINAL, AND A METHOD OF OPERATING A TELECARE-ENABLED MOBILE TERMINAL

(71) Applicant: DORO AB, Lund (SE)

(72) Inventors: Xavier Corbin, Chevreuse (FR); Mattias Nilsson, Lund (SE); Peter Cullin, Staffanstorp (SE); Fredrik Palmqvist, Limhamn (SE)

(73) Assignee: Doro AB, Lund (SE)

( * ) Notice: Subject to any disclaimer, the term of this patent is extended or adjusted under 35 U.S.C. 154(b) by 0 days.

(21) Appl. No.: 15/508,743

(22) PCT Filed: Sep. 3, 2015

(86) PCT No.: PCT/EP2015/070173
§ 371 (c)(1),
(2) Date: Mar. 3, 2017

(87) PCT Pub. No.: WO2016/034681
PCT Pub. Date: Mar. 10, 2016

(65) Prior Publication Data
US 2017/0279954 A1 Sep. 28, 2017

(30) Foreign Application Priority Data

Sep. 3, 2014 (EP) .................................. 14290262

(51) Int. Cl.
*H04B 1/38* (2015.01)
*H04M 1/00* (2006.01)
(Continued)

(52) U.S. Cl.
CPC ........ *H04M 1/72536* (2013.01); *G06F 19/00* (2013.01); *G06F 19/3418* (2013.01);
(Continued)

(58) Field of Classification Search
CPC .. H04M 1/72536; H04M 1/675; H04M 3/436; H04M 2242/04; H04M 2250/14; H04W 88/02; G06F 19/3418
See application file for complete search history.

(56) References Cited

U.S. PATENT DOCUMENTS

2002/0120857 A1* 8/2002 Krishnan ............... H04M 17/02
713/193
2005/0096088 A1* 5/2005 Bae ........................ H04W 12/12
455/558
(Continued)

FOREIGN PATENT DOCUMENTS

WO WO 2007/108811 9/2007
WO WO 2008/117999 10/2008
(Continued)

OTHER PUBLICATIONS

International Search Report for PCT/EP2015/070173, dated Mar. 12, 2015.
(Continued)

*Primary Examiner* — Nguyen T Vo
(74) *Attorney, Agent, or Firm* — Merchant & Gould P.C.

(57) ABSTRACT

A telecare-enabled mobile terminal has a controller, a first subscriber identity and a second subscriber identity. At least one mobile network interface provides telecommunication connectivity for the mobile terminal as identified by the first subscriber identity and the second subscriber identity, respectively. The controller is configured to use the first subscriber identity for outbound telecommunication traffic relating to a telecare service provided by a remote telecare provider. The controller is configured to use the second subscriber identity for outbound telecommunication traffic not relating to the telecare service.

9 Claims, 4 Drawing Sheets

(51) Int. Cl.
  *H04M 1/725* (2006.01)
  *G06F 19/00* (2018.01)
  *H04M 1/675* (2006.01)
  *H04M 3/436* (2006.01)
  *H04W 88/02* (2009.01)

(52) U.S. Cl.
  CPC ........... *H04M 1/675* (2013.01); *H04M 3/436* (2013.01); *H04M 2242/04* (2013.01); *H04M 2250/14* (2013.01); *H04W 88/02* (2013.01)

(56) References Cited

U.S. PATENT DOCUMENTS

| | | | | |
|---|---|---|---|---|
| 2008/0161049 | A1* | 7/2008 | Lagnado | H04W 12/08 455/558 |
| 2010/0255880 | A1 | 10/2010 | Huang et al. | |
| 2012/0142308 | A1* | 6/2012 | Lee | H04W 4/003 455/404.1 |
| 2012/0309341 | A1 | 12/2012 | Ward | |
| 2013/0303112 | A1* | 11/2013 | Chhipa | H04W 12/02 455/405 |
| 2014/0120859 | A1* | 5/2014 | Ekici | H04W 4/22 455/404.1 |
| 2016/0261651 | A1* | 9/2016 | Stille | H04L 65/1076 |

FOREIGN PATENT DOCUMENTS

| | | |
|---|---|---|
| WO | WO 2010/140781 | 12/2010 |
| WO | WO 2012/022276 | 2/2012 |

OTHER PUBLICATIONS

International Preliminary Report on Patentability for PCT/EP2015/070173, dated Nov. 14, 2016.

European Search Report for European Patent Application No. 14290262.6, dated Feb. 26, 2015.

Notice of Allowance for European Patent Application No. 15757293.4, dated Mar. 28, 2018.

\* cited by examiner

TELECARE-ENABLED MOBILE TERMINAL, AND A METHOD OF OPERATING A TELECARE-ENABLED MOBILE TERMINAL

This application is a National Stage Application of PCT/EP2015/070173, filed 3 Sep. 2015, which claims benefit of European Patent Application No. 14290262.6, filed 3 Sep. 2014, which applications are incorporated herein by reference. To the extent appropriate, a claim of priority is made to each of the above disclosed applications.

TECHNICAL FIELD

The present invention generally relates to the field of mobile terminals, and more particularly to telecare-enabled mobile terminals.

BACKGROUND

Mobile terminals appear in many different brands, shapes and types, adapted for use in one or more mobile telecommunications networks like GSM, UMTS, LTE, LTE Advanced, D-AMPS, CDMA2000, FOMA or TD-SCDMA.

In the early days of mobile telecommunications, the mobile terminals were used for speech communication only. The situation has of course changed dramatically since then. Nowadays, mobile terminals are also frequently used for professional, personal and recreational services and thus contain a plurality of application programs such as call handling, calendar, messaging, word processing, www browsing, etc. Such services and application programs are collectively referred to as mobile services in this document.

In recent years, mobile terminals have been introduced which are specifically adapted for use with telecare services. Broadly speaking, telecare is about offering remote care of elderly or physically less able people, providing the care and reassurance needed to allow them to remain living in their own homes. In the present invention, a mobile terminal is the tool used by an individual being remotely cared for. The telecare services may, for instance, involve any of the following: assistance, attendance, medical care, emergency service or rescue of the individual. It shall therefore be explicitly noticed that in the present invention, telemedicine services and/or telehealth services may be included in the notion telecare.

The present inventors have identified some drawbacks with existing telecare-enabled mobile terminals. One such identified drawback is that from the telecare provider's point of view, the provider is dependent on the user of the mobile terminal to order, pay for, renew and maintain a mobile network subscription. However, since the typical user of a telecare-enabled mobile terminal is an elderly, technically inapt and potentially disordered person, there is a risk that the user will in fact not duly attend to the mobile network subscription. A risk of impairment in operational security and reliability for the telecare service is therefore at hand.

The international application WO2012022276 discloses a set of units able to communicate one with each other by means of cooperating software, mutually control themselves and imagine displays from other units. Invention enables by means of indicated set or individual units as well, to make remote monitoring of persons and control their location, heath condition and capacity. Also, it enables to monitored persons to check their condition on mobile unit.

A wireless communication device, a method, and a computer program product that enable multiple subscriber numbers to be concurrently assigned to and supported within a single communication device, such as a wireless/cellular phone is described in the international application WO2007108811. The communication device is designed with circuit components and logic that allows two or more subscriber numbers to be concurrently programmed into the device. Each subscriber number is individually supported, with the logic also providing some overlapping functionality. A user selectively utilizes one of the subscriber numbers to originate a new call out and/or accept an incoming call to that subscriber number and may toggle between subscriber numbers to communicate on.

The international application WO2010140781 discloses a dual SIM terminal and an operating method thereof for supporting dual standby and single talk using a single baseband. The dual SIM mobile terminal may include a controller which is a single chipset, a dual SIM, and two radio frequency (RF) units, thereby having an effect capable of providing a service at the same level as a dual SIM using two mobile terminals even with one mobile terminal. Furthermore, dual SIM switching is performed according to a state of the network, a pricing system, and a user's setting, thereby providing the user's desired service.

Moreover, the present inventors have realized that a further risk of impairment in operational security and reliability for the telecare service comes from the fact that the user may—inadvertently—choose a mobile network subscription which is technically unsuitable for the telecare service(s) in terms of technical performance, signal coverage, or service availability.

SUMMARY

It is accordingly an object of the invention to eliminate or alleviate at least some of the problems referred to above and, generally, offer an improvement in terms of operational security and reliability for telecare services in a telecare-enabled mobile terminal.

A first aspect of the present invention is a telecare-enabled mobile terminal comprising:
  a controller;
  a first subscriber identity;
  a second subscriber identity; and
  at least one mobile network interface for providing telecommunication connectivity for the mobile terminal as identified by the first subscriber identity and the second subscriber identity, respectively.

The controller is configured to use the first subscriber identity at least for outbound telecommunication traffic relating to a telecare service provided by a remote telecare provider, and the controller is configured to use the second subscriber identity at least for outbound telecommunication traffic not relating to said telecare service.

A telecare-enabled mobile terminal with improved operational security and reliability for telecare services is thereby provided.

As used in this document, the term "outbound telecommunication traffic" refers to mobile terminal-originating telecommunication traffic. A communication session involving such outbound telecommunication traffic thus starts at, or is initiated by, the mobile terminal; once the session has been initiated, the communication may be bidirectional between the mobile terminal and its communication party, such as a telecare provider of said telecare service. Hence, the controller is configured to use the first subscriber identity for outbound telecommunication traffic relating to a telecare service provided by a remote telecare provider, wherein the outbound telecommunication traffic belongs to a communication session having started at, or having been initiated by, the mobile terminal.

The telecare service may, preferably but not necessarily, be one or more of the following: assistance from a telecare provider of said telecare service to a user of said mobile terminal, attendance of said user by said telecare provider, medical care of said user by said telecare provider, and emergency or rescue action to relieve said user in a critical situation.

Preferably but not necessarily, the outbound telecommunication traffic relating to said telecare service may be one or more of the following: an assistance request by said user, user behavior monitoring data generated or conveyed by said mobile terminal, user medical status data generated or conveyed by said mobile terminal, and an alarm notification generated or conveyed by said mobile terminal.

In one or more embodiments, the controller is configured to: detect a selective action by said user in a user interface of said mobile terminal (such as actuation of an assistance button of said mobile terminal (for instance in the form of a physical (mechanical) button, or a virtual button in a graphical user interface of the mobile terminal)), generate an assistance request in response to the detected action, and use the first subscriber identity to send the assistance request as data traffic to the telecare provider of said telecare service.

In this or these embodiments, the controller may be further configured to enter an assistance request mode in response to the detected action. When an inbound call is received to the mobile terminal while in assistance request mode, the controller may determine if the inbound call is from any of the following: a telecare provider of said telecare service, an emergency service, or a person on a list of related persons. If so, the controller will accept the call, otherwise it will decline the call.

In one or more embodiments, the controller is configured to handle an inbound call according to a prioritization scheme by: accepting an inbound call to the second subscriber identity if there is no ongoing call for the first subscriber identity, declining an inbound call to the second subscriber identity if there is an ongoing call for the first subscriber identity, and terminating an ongoing call for the second subscriber identity upon arrival of an inbound call to the first subscriber identity and accepting the inbound call to the first subscriber identity.

As used herein, a "call" may be a circuit-switched or packet-switched (IP-based) voice call, or a circuit-switched or packet-switched (IP-based) video call.

In one or more embodiments, the controller is configured to: determine if the mobile terminal has telecommunication connectivity to a mobile telecommunication network for the first subscriber identity, and, if not, use the second subscriber identity for the outbound telecommunication traffic relating to said telecare service.

Alternatively, in one or more embodiments, the controller is configured to: determine if the mobile terminal has telecommunication connectivity to a mobile telecommunication network for the first subscriber identity, and, if not, use the second subscriber identity to send a notification to a telecare provider of said telecare service.

In one or more embodiments, the controller is configured to: prevent a user of the mobile terminal from selecting the first subscriber identity for usage for outbound telecommunication traffic which does not relate to said telecare service.

A second aspect of the present invention is a method of operating a telecare-enabled mobile terminal. The method comprises: providing a first subscriber identity for telecommunication connectivity with a mobile telecommunication network, providing a second subscriber identity for telecommunication connectivity with a mobile telecommunication network, using the first subscriber identity for outbound telecommunication traffic relating to a telecare service provided by a remote telecare provider, and using the second subscriber identity for outbound telecommunication traffic not relating to said telecare service.

A method of operating a telecare-enabled mobile terminal with improved operational security and reliability for telecare services is thereby provided.

The method according to the second aspect may have the same features as any or all of the embodiments of the mobile terminal according to the first aspect, and/or one or more features which functionally correspond to one or more structural features of any or all of the embodiments of the mobile terminal according to the first aspect.

Embodiments of the invention are defined by the appended dependent claims and are further explained in the detailed description section.

It should be emphasized that the term "comprises/comprising" when used in this specification is taken to specify the presence of stated features, integers, steps, or components, but does not preclude the presence or addition of one or more other features, integers, steps, components, or groups thereof. All terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

Objects, features and advantages of embodiments of the invention will appear from the following detailed description, reference being made to the accompanying drawings, in which:

FIG. 2b is an enlarged schematic block diagram of a part of the Dual SIM mobile terminal shown in FIG. 2a.

DETAILED DESCRIPTION

Figure 1:
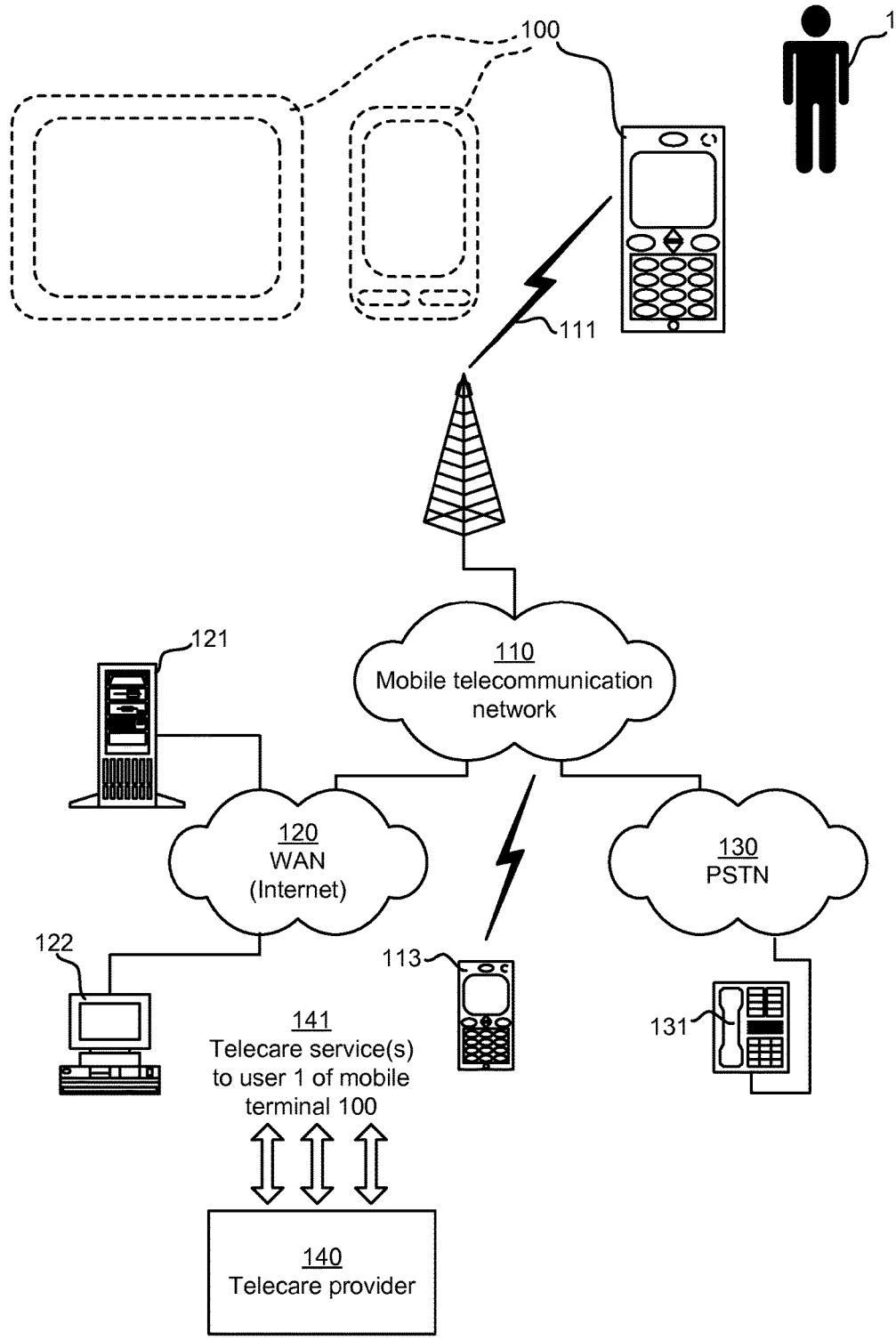
FIG. 1 is a schematic illustration of a non-limiting example of a telecommunication system in which a telecare-enable mobile terminal of the present invention may be operated.

Embodiments of the invention will now be described with reference to the accompanying drawings. The invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular embodiments illustrated in the accompanying drawings is not intended to be limiting of the invention. In the drawings, like numbers refer to like elements.

Before turning to a detailed description of the disclosed embodiments, an exemplifying environment in which they may be exercised will now be briefly described with reference to FIG. 1.

In FIG. 1, a portable electronic device in the form of a mobile terminal 100 is part of a cellular telecommunication system. The mobile terminal 100 may connect to a mobile telecommunication network 110 over a radio link 111 and a base station 112. The mobile terminal 100 and the mobile telecommunication network 110 may comply with any commercially available mobile telecommunication standard, for instance (without limitation) GSM, UMTS, LTE, LTE Advanced, D-AMPS, CDMA2000, FOMA and TD-SCDMA. Embodiments of the mobile terminal 100 will be described in more detail with reference to the following drawings.

A public switched telephone network (PSTN) 130 is connected to the mobile telecommunication network 110. Telephone terminals of PSTN subscribers may connect to the PSTN 130. In FIG. 1, a stationary telephone 131 is indicated as a mere example of this.

The mobile telecommunication network 110 is operatively associated with a wide area data network 120, which may be the Internet or a part thereof. Server computers 121 and client computers 122 may be connected to the wide area data network 120 to allow communication with the mobile terminal 100. The mobile terminal 100 may also communicate with other mobile terminals 113 over the mobile telecommunication network 110.

A user 1 of the mobile terminal 100 may use different mobile services, such as voice calls, Internet browsing, video calls, data calls, facsimile transmissions, still image transmissions, video transmissions, electronic messaging, multimedia streaming, gaming, and e-commerce. The invention is however not limited to any particular set of services, except telecare services which are central to the inventive aspects of the mobile terminal 100. As seen in FIG. 1, one or more telecare services 141 are provided by a telecare provider 140 to the user 1 of the mobile terminal 100. When providing the telecare services 141, the telecare provider 140 and its personnel may use devices like any of the aforementioned ones which are indicated at 113, 121, 122 and 131 in FIG. 1.

The mobile terminal 100 is a Dual SIM terminal. As is known per se, Dual SIM (Subscriber Identity Module) terminals have been introduced during recent years. Dual SIM enables a user to insert not only one SIM card in the mobile terminal 100, but in fact two SIM cards. In effect, this will provide the mobile terminal 100 with two subscriber identities, each generally speaking being capable of performing mobile services using the respective inserted SIM.

At power-on, both SIMs of the mobile terminal 100 may perform an IMSI (International Mobile Subscriber Identity) attach, either to the same mobile telecommunication network 110, or to different mobile telecommunication networks. For ease of reading, the description in this document will refer to the mobile telecommunication network 110 in singular; there may however just as well be two different networks (one of which may be the network 110).

As there are two SIMs available, there will be two unique IMSIs as well for the mobile terminal 100. From the point of view of the mobile telecommunication network 110, the mobile terminal 100 is seen as two different terminals. From the perspective of the user 1, Dual SIM allows the user to replace two different mobile terminals by a single mobile terminal 100. Once the two IMSIs have been attached, according to the invention, the handling of mobile services is differentiated in a way such that a telecare service provided by a remote telecare provider is confined to the first SIM, whereas other (non-telecare) services are confined to the second SIM. This differentiation will be described in more detail later in this document.

One kind of Dual SIM is referred to as DSDS (Dual SIM Dual Standby; sometimes referred to as Dual SIM standby phones). In a DSDS mobile terminal, when one of the SIMs is involved in an active connection (referred to as the primary SIM), the other SIM (secondary SIM) will be inactive.

Another kind of Dual SIM is referred to as DSDC (Dual SIM Dual Connectivity or Dual SIM Dual Call; sometimes referred to as Dual SIM Dual Active (DSDA)). Different from DSDS, a DSDC (or DSDA) mobile terminal is able to have simultaneously ongoing active connections on the different SIMs. To this end, the mobile network interface to the mobile telecommunication network 100 will be duplicated in a DSDC mobile terminal.

The mobile terminal 100 is not limited to any particular kind when it comes to physical design. It may, for instance, be of a well-known kind which comprises a keypad (such as an ITU-T or PIN type keypad, having keys representing digits "0" through "9" as well as signs "*" and "#", and operation keys such as a YES/OK/CALL key and a NO/CANCEL/HANGUP key) as the primary input device for interaction with the user 1, and a display (such as a non-touch display or a touch-sensitive display) as the primary output device for interaction with the user 1. Such mobile terminals are sometimes referred to as "feature phones". The mobile terminal 100 shown with solid lines in the uppermost part of Fig is illustrated as a feature phone. Feature phones may consist of a single housing (the type sometimes being referred to as monoblock), or they may have two main housing parts hinged together to form a clamshell phone or a swivel phone.

Alternatively, the mobile terminal 100 may for instance be a smartphone or a tablet computer, as illustrated with broken lines in the uppermost part of FIG. 1. As is well known, a smartphone or a tablet computer typically has a touch-sensitive display being the primary input device as well as the primary output device for interaction with the user 1.

The mobile terminal 100 may have various other elements, such as microphone, loudspeaker, camera, power switch, battery, charger interface, accessory interface, volume controls, and antenna. Such elements are utterly well known to the skilled person and do not require any specific description.

Figure 2A:
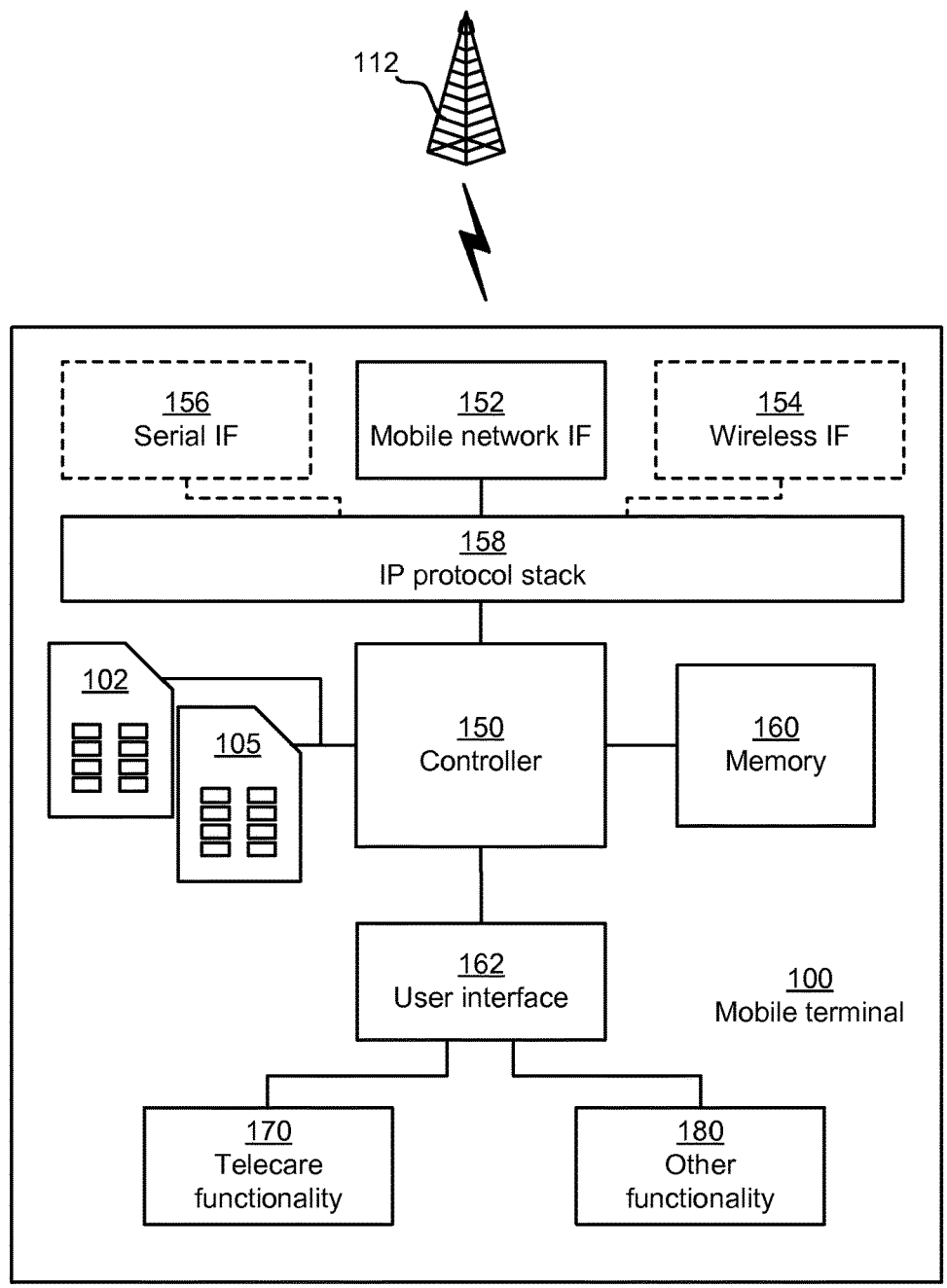
FIG. 2a is a schematic block diagram of a Dual SIM mobile terminal enabled for telecare services according to an embodiment of the present invention.
Figure 2A:

Some primary components of the Dual SIM mobile terminal 100 are seen in FIG. 2a. The mobile terminal 100 has a controller 150 which has the overall responsibility for controlling the operation of the terminal 100. In the disclosed embodiment, the controller 150 is a central processing unit (CPU), but it can alternatively be a digital signal processor (DSP), or other programmable electronic logic device such as an application-specific integrated circuit (ASIC) or field-programmable gate array (FPGA). The controller 150 is coupled to a memory 160 which may comprise a work memory and a storage memory. The memory 160 may for instance be implemented in the form of RAM, EEPROM, flash memory (e.g. memory card), magnetic hard disk, or any combination thereof. The memory 160 is capable of storing program code which is executable by the controller 150 so as to cause performing of the functionality of the mobile terminal 100 as described in various parts of this document. In alternative embodiments, some or all of the functionality of the mobile terminal 100 may instead be performed by dedicated hardware.

The Dual SIM mobile terminal 100 has a mobile network interface 152 which allows the terminal 100 to communicate with the mobile telecommunication network 110. The mobile network interface 152 comprises an internal or external antenna as well as appropriate radio circuitry for establishing and maintaining a wireless link to a nearby base station in the mobile telecommunication network 110 (e.g. link 111 and base station 112 in FIG. 1). The radio circuitry comprises a radio receiver and transmitter (transceiver; TX/RX), containing elements like band pass filters, amplifiers, mixers, local oscillators, low pass filters, AD/DA converters, etc.

For embodiments where the Dual SIM mobile terminal 100 is a DSDC mobile terminal, the mobile network interface 152 to the mobile telecommunication network 110 may be duplicated, as already mentioned.

In addition, the Dual SIM mobile terminal 100 may have a wireless interface 154 which may be adapted for communication in accordance with one or more short-range wireless communication standards such as Bluetooth, WiFi (e.g. IEEE 802.11, wireless LAN), Near Field Communication (NFC), or Infrared Data Association (IrDA). A serial interface 156, such as USB, may also be provided to allow the mobile terminal 100 to communicate over a serial cable with for instance a personal computer. Such interfaces 154, 156 may be absent in some embodiments.

An IP protocol stack 158 is provided to allow packet-based IP data communication via the mobile network interface 152 (and the interfaces 154, 156 when applicable).

A user interface 162 allows the user 1 to interact with the mobile terminal 100. As already referred to in conjunction with FIG. 1, the user interface 162 includes display means, such as at least one LCD or LED display (see 162a in FIG. 3), as well as input means for the user 1 (see 162b in FIG. 3). The input means may e.g. include a keypad with alphanumeric keys and/or other keys such as arrow keys (navigation keys) and functional keys (soft keys), and/or a joystick, touch pad, rotator, jog dial, etc. The display means and input means may be jointly realized by a touch-sensitive display in some embodiments (see 162c in FIG. 3). The user interface 162 typically also involves a loudspeaker and a microphone, as well as a dedicated alarm button.

Figure 2B:
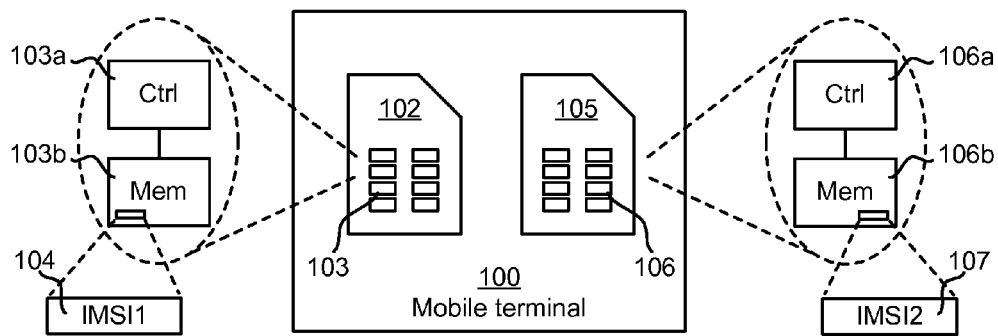

With reference to FIG. 2b, the Dual SIM mobile terminal 100 has a first SIM reader capable of accessing a first SIM card 102, and a second SIM reader capable of accessing a second SIM card 105. The first SIM card 102 comprises electronic circuitry 103 which constitutes a local SIM controller 103a and a memory 103b. The memory 103b has a memory area 104 for storing the first subscriber identity in the form of a first IMSI number, IMSI1. Conversely, the second SIM card 105 comprises electronic circuitry 106 which constitutes a local SIM controller 106a and a memory 106b. The memory 106b has a memory area 107 for storing the second subscriber identity in the form of a second IMSI number, IMSI2.

In addition, any of the first and/or second SIM memories 103b, 106b may store commands or program instructions for providing value-added services, for instance in the form of an increased level of security through identity verification and encryption measures which serve to provide secure transactions. Such commands or program instructions in the SIM memories 103b, 106b may for instance be in compliance with any of the SIM Application Toolkit (STK), USIM Application Toolkit (USAT) or Card Application Toolkit (CAT) standards.

Reference is now again made to FIG. 2a. Via the user interface 162, the user 1 may access telecare functionality 170 provided in, by or through the mobile terminal 100. Also, via the user interface 162, the user 1 may access various other functionality 180 provided in, by or through the mobile terminal 100.

The telecare functionality 170 may involve any of the following typical telecare services 141 provided by the telecare provider 140:

Assistance to the User 1

When the user 1 finds himself in need of assistance, he may contact the telecare provider 140 by way of an assistance request. The user 1 may initiate the assistance request by a selective action in the user interface 162 of the mobile terminal. The selective action may typically be the actuation of a dedicated assistance button being part of the input means 162b of the mobile terminal 100. When the mobile phone 100 is a feature phone, the dedicated assistance button may typically take the form of a physical (mechanical) button. When the mobile phone 100 is a smartphone or a tablet computer, the dedicated assistance button may typically take the form of a virtual button in a graphical user interface on the touch-sensitive display 162c of the mobile terminal 100. Alternatively or additionally, the dedicated assistance button may take the form of a physical (mechanical) button also when the mobile phone 100 is a smartphone or a tablet computer.

The controller 150 will then generate an assistance request in response to the detected action. The assistance request may be sent as data traffic to the telecare provider 140 of the telecare service 141. The assistance request may include information to identify the mobile terminal 100 and/or the user 1. The assistance request may also include information about date and time, and/or location information retrieved for instance from a satellite (GPS) receiver in the mobile terminal 100. Since this outbound telecommunication traffic relates to a telecare service, the first subscriber identity (IMSI1) will be used for this transmission.

Attendance of the User 1

The user's behavior may be monitored by the telecare provider 140. Sensors internal or external to the mobile terminal 100 may be used. For instance, an internal accelerometer may be used to detect a sudden fall of the user 1, or prolonged immobility of the user 1. This may be a useful telecare service 141 particularly for an individual suffering from illness or physical weakness.

A satellite (GPS) receiver in the mobile terminal 100 may be used for geofencing purposes to detect when the user 1 exits a permitted zone. This may be a useful telecare service 141 particularly for a disoriented individual suffering for instance from dementia or Alzheimer's disease.

The mobile terminal may receive sensor data or instructions from external equipment via the interfaces 154 or 156. Such equipment may for instance include a video camera, door sensor, smoke detector, etc.

The resulting user behavior monitoring data from such internal or external sensors or equipment may be sent as data traffic to the telecare provider 140 of the telecare service 141, possibly after certain preprocessing or decision making already in the mobile terminal 100. Again, since this outbound telecommunication traffic relates to a telecare service, the first subscriber identity (IMSI1) will be used for this transmission.

Medical Care of the User 1

The user's medical status may be taken care of by the telecare provider 140. Sensors or equipment internal or external to the mobile terminal 100 may be used, such as a blood pressure measuring device, a blood glucose measuring sensor, a body temperature sensor, a cardiac activity measuring device, etc.

The resulting user medical status data from such internal or external sensors or equipment may be sent as data traffic to the telecare provider 140 of the telecare service 141, possibly after certain preprocessing or decision making already in the mobile terminal 100. Again, since this outbound telecommunication traffic relates to a telecare service, the first subscriber identity (IMSI1) will be used for this transmission.

Emergency or Rescue Action to Relieve the User 1 in a Critical Situation

If the user 1 finds himself to be in a critical situation, or if a conclusion to this end is reached as a result of any of the services referred to above, an emergency or rescue action may be needed. Depending on implementation and preference, it may be initiated from the telecare provider 140 of the telecare service 141, or from the mobile terminal itself. In the latter case, an alarm notification may be generated by the mobile terminal 100 or user 1, and sent as outbound telecommunication traffic to the telecare provider 140 of the telecare service 141. Again, since this outbound telecommunication traffic relates to a telecare service, the first subscriber identity (IMSI1) will be used for this transmission.

Figure 3:
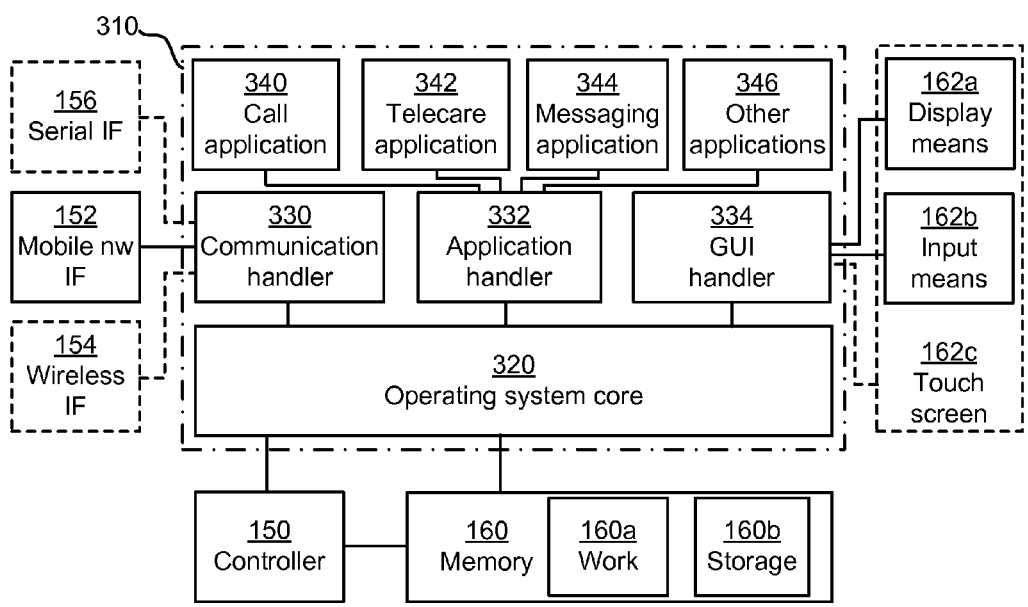
FIG. 3 is a schematic block diagram illustrating the basic internal hardware and software layout of the mobile terminal shown in FIGS. 2a, 2b and 3.

Reference is now made to FIG. 3 for a description of the internal software and hardware structure of the Dual SIM mobile terminal 100. Software components are indicated within a dash-dotted frame 310, whereas hardware components are outside of this frame. The mobile terminal 100 has the aforementioned controller 150, being responsible for general device operations. Any commercially available central processing unit (CPU) or digital signal processor (DSP), or other programmable electronic logic device such as an application-specific integrated circuit (ASIC) or field-programmable gate array (FPGA), may be used to implement the controller 150. The controller 150 has the aforementioned associated memory 160 which includes a work memory (RAM) 160a and a non-volatile storage memory 160b, for instance in the form of EEPROM, flash memory (e.g. memory card), hard disk, or any combination thereof. The controller 150 uses the memory 160 for different purposes, for instance for storing file objects as well as data and program instructions for the software in the mobile terminal 100.

The software includes an operating system core 320 on a lower level, application programs 340-346 on an upper level for interaction with the user 1, and drivers and handlers for the hardware and the application programs on an intermediate level. The intermediate level includes a GUI handler 334 which forms the user interface 162 (FIG. 2a) towards the user 1 by controlling the display 162a and the input means 162b, as well as other I/O devices which may be included in the mobile terminal 200/250 (e.g. microphone, loudspeaker, vibrator, ringtone generator, LED status indicator, audio volume controls, dedicated assistance button, etc). When the display 162a is a touch-sensitive display 162c, the GUI handler 334 controls the touch-sensitive display 162c to act both as a display means and as an input means.

An application handler 332 controls the application programs 340-346, which may include a call handling (e.g. voice calls, video calls) application 340, a telecare application 342, a messaging (e.g. SMS, MMS, email, chat) application 344, as well as various other applications 346, such as applications for calendar, contacts, web browser, file handling, a control panel or settings application, a camera application, one or more video games, a word processing application, a spreadsheet application, a drawing application, a slideshow presentation application, a multimedia streaming application, etc.

The call handling application 340 may include any of the following functionality:
   Initiating, conducting and closing outbound (mobile-originated) telephone calls (e.g. voice calls, video calls)
   Receiving, conducting and closing inbound (mobile-terminated) telephone calls
   Accessing call logs
   Creating or updating contact records in the mobile terminal 100

The calls may be conventional circuit-switched calls conveyed over the mobile telecommunication network 110 and possibly the PSTN 130, or packet-switched calls conveyed over the mobile telecommunication network 110 and possibly the PSTN 130, or IP-based calls conveyed over wide area network 120 while using the mobile telecommunication network 110 merely as a transport channel for the IP traffic.

The telecare functionality 180 referred to in FIG. 2a may be implemented by the telecare application 342. In addition, applications other than the telecare application 342, such as the messaging application 344 and the call handling application 340, may implement parts of the telecare functionality 180 of the mobile terminal 100. In some embodiments, no separate application is provided to implement the telecare functionality 180 of the mobile terminal 100; in such a case the telecare functionality 180 may be implemented entirely by functions within the applications 340-346.

The software also includes various modules, protocol stacks, drivers, etc., which are commonly designated as communication handler 330 and which provide communication support for the mobile network interface 152 and, when applicable, the wireless interface 154 and/or the cellular interface 156.

Figure 4:
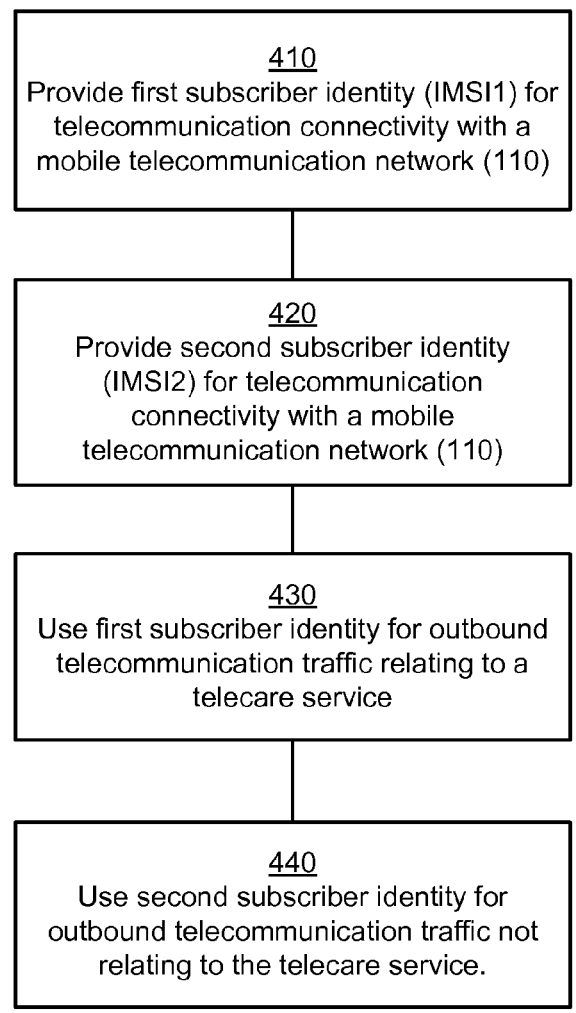
FIG. 4 is a schematic flowchart diagram illustrating a method according to the present invention.

Reference is now made to FIG. 4, which illustrates telecommunication traffic differentiation according to the present invention. The mobile terminal 100 is, as already described, provided with the first subscriber identity, IMSI1, for telecommunication connectivity with the mobile telecommunication network 110; see step 410. Moreover, the mobile terminal 100 is provided with the second subscriber identity, IMSI2, for telecommunication connectivity with a mobile telecommunication network 110; see step 420. As seen in step 430, (at least) outbound telecommunication traffic which relates to a telecare service provided by a remote telecare provider is confined to the first subscriber identity, IMSI1. On the other hand, as seen in step 440, (at least) outbound telecommunication traffic relating other (non-telecare) services is confined to the second subscriber identity, IMSI2.

Some preferred examples of such differentiation will now described, in addition to the ones already given in the preceding description.

Example 1—Blocking of Inbound Calls Except from Telecare Provider when an Assistance Request has been Made When the controller 150 (for instance running the telecare application 342) has detected that the user 1 has made the selective action in the user interface 162 of the mobile terminal (e.g. actuation of the dedicated assistance button), it may in response enter an assistance request mode. While in assistance request mode, when an inbound call is received to the mobile terminal 100, the controller 150 may determine if the inbound call is from any of the following:

the telecare provider 140 of the telecare service 141, an emergency service; and a person on a list of related persons. (Such a list may represent relatives, friends or other supporting people to the user 1 and may be stored in the mobile terminal 100).

If the controller 150 determines that the inbound call is indeed from any of the entities above, it will accept the call. Otherwise, it will decline the call.

This will increase the security to the user 1 and the reliability of the telecare service 141, since an unfortunate situation is avoided where an accidental, unrelated call might arrive to the mobile terminal 100 before the telecare provider has been able to respond to the attendance request by way of a call to the mobile terminal 100. The blocking may be done for inbound calls to the first subscriber identity, IMSI1, and/or for inbound calls to the second subscriber identity, IMSI2.

Example 2—Enhancing the Availability for Incoming Telecare Service Calls

The controller 150 may be configured to handle an inbound call to the mobile terminal 100 according to a prioritization scheme as follows:

An inbound call to the second subscriber identity, IMSI2, is accepted if there is no ongoing call for the first subscriber identity, IMSI1.

An inbound call to the second subscriber identity, IMSI2, is declined if there is an ongoing call for the first subscriber identity, IMSI1.

An ongoing call for the second subscriber identity, IMSI2, is terminated upon arrival of an inbound call to the first subscriber identity, IMSI1, while accepting the inbound call to the first subscriber identity.

In this way, the second subscriber identity, IMSI2, is available for non-telecare incoming calls at any time except when the first subscriber identity, IMSI1, is needed for a telecare incoming call. This represents a user friendly but still secure and reliable solution.

Example 3—Enhanced Telecare Operability by Using the Second Subscriber Identity as Backup for Telecare Services in Case of Unavailability of the First Subscriber Identity The controller 150 may be configured to determine if the mobile terminal 100 has telecommunication connectivity 111 to the mobile telecommunication network 110 for the first subscriber identity, IMSI1. A lack of telecommunication connectivity 111 can for instance be due to a temporary failure at the operator of the first subscriber identity in the mobile telecommunication network 110 (if different from the operator of the second subscriber identity), or with the radio access technology (RAT) used for the first subscriber identity (if different from the RAT of the second subscriber identity). A lack of telecommunication connectivity 111 can alternatively be due the fact that the SIM card 102 of the first subscriber identity has been damaged, removed from or never inserted in the SIM card reader in the mobile terminal 100, or simply that the first subscriber identity is temporarily out of reach for the mobile telecommunication network 110 (currently not within the cell of any base station in the network 110).

If it is determined that telecommunication connectivity 111 to the mobile telecommunication network 110 is lacking for the first subscriber identity, IMSI1, the controller 150 may use the second subscriber identity, IMSI2, for the outbound telecommunication traffic relating to the telecare service. Hence, a backup communication channel for the telecare service traffic is provided.

Alternatively, the controller 150 may be configured to determine if the mobile terminal 100 has telecommunication connectivity 111 to the mobile telecommunication network 110 for the first subscriber identity, IMSI1. If not, the controller 150 may use the second subscriber identity, IMSI2, to send a notification to the telecare provider 140 of said telecare service 141. Hence, the telecare provider 140 will be informed of the situation that the first subscriber identity, IMSI1, is not available for use, and may take appropriate action. Such action may involve sending out personnel to help the user 1 in remedying the failure situation, or sending a command to the mobile terminal 100 instructing it to switch to single-SIM operation (i.e. IMSI2) for all services—telecare services as well as other services.

Alternatively or additionally, the controller 150 may be configured to provide a backup for incoming calls from the telecare provider 140 in a situation when it has been determined that telecommunication connectivity 111 to the mobile telecommunication network 110 is lacking for the first subscriber identity, IMSI1. In such a case, the controller 150 may use the second subscriber identity, IMSI2, to send a request to the mobile telecommunication network 110 to enable call forwarding for inbound calls to the first subscriber identity, IMSI1, to be forwarded to the second subscriber identity, IMSI2.

Example 4—Preventing Improper Usage of at Least the First Subscriber Identity

The controller 150 may be configured to prevent the user 1 of the mobile terminal 100 from selecting the first subscriber identity, IMSI1, for usage for anything but outbound telecommunication traffic relating to the telecare service 141. Hence, even if the user 1 attempts to use the first subscriber identity, IMSI1, for other mobile services than telecare services 141, the controller 150 will prevent him from doing so. This will increase the operational security and reliability of the telecare service 141.

Usage of the first subscriber identity, IMSI1, for anything but outbound telecommunication traffic relating to the telecare service 141 may be prevented in various different ways, as is readily realized per se by the skilled person. For instance, the telecare functionality 170 (e.g. the telecare application 342) may be the only functionality in the mobile terminal 100 that has access to the first subscriber identity, IMSI1, whereas for all other functionality 180 (e.g. the applications 340, 344, 346) only the second subscriber identity, IMSI2, is accessible while the first subscriber identity, IMSI1, is inaccessible. In other words, the mobile terminal 100 is programmed such that the first subscriber identity, IMSI1, is only "visible" to the telecare functionality 170 (e.g. the telecare application 342), whereas the second subscriber identity, IMSI2, is "visible" to the non-telecare functionality 180 (e.g. the applications 340, 344, 346).

Correspondingly, usage of the second subscriber identity, IMSI2, for outbound telecommunication traffic relating to the telecare service 141 may be prevented in similar ways (subject to exceptions for embodiments which use the backup functionality referred to above in Example 3).

Moreover, measures may be taken for preventing the user 1 from switching positions of the first and second SIM cards 102, 105 in the first and second SIM readers, which could otherwise have the effect of allowing usage of the second subscriber identity, IMSI2, for outbound telecommunication traffic relating to the telecare service 141 and/or the first subscriber identity, IMSI1, for anything but outbound telecommunication traffic relating to the telecare service 141.

For instance, in one embodiment, SIM PIN lock functionality is enabled for at least the first SIM card 102, and possibly also for the second SIM card 105. The first SIM card 102 will typically be provided by the remote telecare provider 140, or an agent acting on behalf thereof; hence, the remote telecare provider 140 has initial control of the first SIM card 102 and may therefore enable SIM PIN lock functionality and set a PIN (personal identification number) which is not known to the user 1. The SIM PIN lock functionality of this embodiment may be configured such that the PIN will have to be entered when the SIM card is moved to the other SIM reader (or another device), but not each time the mobile terminal 100 is powered on.

In this or another embodiment, the controller 150 of the mobile terminal 100 is configured to read the first subscriber identity IMSI1 (and possibly also the second subscriber identity IMSI2) when the mobile terminal 100 is powered on for the first time, and store the read IMSI1 as a reference IMSI in a secret area of the local memory 160 (or alternatively in a remote memory). Then, every time a change of SIM cards occurs in the first SIM reader, the controller 150 will fetch the stored reference IMSI and compare it to the currently read IMSI from the SIM card 102 currently inserted into the first SIM reader. If the matching fails, the controller 150 may block any further usage of the current SIM card 102 in the first SIM reader.

In another embodiment, the first SIM reader is designed with a physical/mechanical SIM card securing mechanism which allows one-time insertion of a SIM card in the first SIM reader but either prevents removal of the SIM card or deliberately damages the SIM card when removed. Alternatively, the damage of the SIM card upon removal thereof from the first SIM reader may be made by the controller 150 on a logical level by, for instance, locking the SIM card with a random PIN or rendering the SIM card inoperable by writing garbage data into the SIM memory 103*b*.

The invention has been described above in detail with reference to embodiments thereof. However, as is readily understood by those skilled in the art, other embodiments are equally possible within the scope of the present invention, as defined by the appended claims.

The invention claimed is:

1. A telecare-enabled mobile terminal comprising:
    a controller;
    a first subscriber identity;
    a second subscriber identity;
    at least one mobile network interface for providing telecommunication connectivity for the mobile terminal as identified by the first subscriber identity and the second subscriber identity, respectively; and
    a first Subscriber Identity Module reader for a first Subscriber Identity Module card storing the first subscriber identity and a second Subscriber Identity Module reader for a second Subscriber Identity Module card storing the second subscriber identity;
    wherein the controller is configured to use the first subscriber identity for outbound telecommunication traffic relating to a telecare service provided by a remote telecare provider,
    wherein the controller is configured to use the second subscriber identity for outbound telecommunication traffic not relating to said telecare service,
    wherein the controller is configured to prevent a user of the mobile terminal from selecting the first subscriber identity for usage for outbound telecommunication traffic which does not relate to said telecare service, and
    wherein the controller is configured to prevent the user from selecting the first subscriber identity by preventing the user from switching positions of the first and second Subscriber Identity Module cards in the first and second Subscriber Identity Module readers.

2. The mobile terminal according to claim 1, further comprising a telecare application and one or more non-telecare applications, wherein the controller is configured to prevent the user from selecting the first subscriber identity by making the first subscriber identity accessible to the telecare application but inaccessible to the one or more non-telecare applications.

3. The mobile terminal according to claim 1, wherein the controller is configured to:
    read the first subscriber identity from the first Subscriber Identity Module card when the mobile terminal is powered on for a first time and store the read first subscriber identity as a reference subscriber identity in a memory;
    upon a change of Subscriber Identity Module cards in the first Subscriber Identity Module reader, fetch the stored reference subscriber identity and compare it to a current subscriber identity read from a current Subscriber Identity Module card in the first Subscriber Identity Module reader; and
    in case of a matching failure of the comparison, block further usage of the current Subscriber Identity Module card in the first Subscriber Identity Module reader.

4. The mobile terminal according to claim 1, wherein said telecare service is one or more of the following:
    assistance from a telecare provider of said telecare service to a user of said mobile terminal,
    attendance of said user by said telecare provider,
    medical care of said user by said telecare provider, and
    emergency or rescue action to relieve said user in a critical situation.

5. The mobile terminal according to claim 4, wherein said outbound telecommunication traffic relating to said telecare service is one or more of the following:
    an assistance request by said user,
    user behavior monitoring data generated or conveyed by said mobile terminal,
    user medical status data generated or conveyed by said mobile terminal, and
    an alarm notification generated or conveyed by said mobile terminal.

6. The mobile terminal according to claim 5, wherein the controller is configured to:
    detect a selective action by said user in a user interface of said mobile terminal;
    generate an assistance request in response to the detected action; and
    use the first subscriber identity to send the assistance request as data traffic to the telecare provider of said telecare service.

7. The mobile terminal according to claim 6, wherein the controller is further configured to:
- enter an assistance request mode in response to the detected action;
- when an inbound call is received to the mobile terminal while in assistance request mode:
  - determine if the inbound call is from any of the following:
    - a telecare provider of said telecare service;
    - an emergency service; and
    - a person on a list of related persons;
  - if so, accept the call; and
  - otherwise, decline the call.

8. The mobile terminal according to claim 1, wherein the controller is configured to:
- determine if the mobile terminal has telecommunication connectivity to a mobile telecommunication network for the first subscriber identity; and, if not:
- use the second subscriber identity for the outbound telecommunication traffic relating to said telecare service.

9. The mobile terminal according to claim 1, wherein the controller is configured to:
- determine if the mobile terminal has telecommunication connectivity to a mobile telecommunication network for the first subscriber identity; and, if not:
- use the second subscriber identity to send a notification to a telecare provider of said telecare service.

* * * * *

UNITED STATES PATENT AND TRADEMARK OFFICE
CERTIFICATE OF CORRECTION

PATENT NO. : 10,178,217 B2
APPLICATION NO. : 15/508743
DATED : January 8, 2019
INVENTOR(S) : Xavier Corbin et al.

Page 1 of 1

It is certified that error appears in the above-identified patent and that said Letters Patent is hereby corrected as shown below:

On the Title Page

Item (71) Applicant: "Doro AB, Lund (SE)" should be -- Doro AB, Malmö (SE) --

Signed and Sealed this
Sixteenth Day of April, 2019

Andrei Iancu
*Director of the United States Patent and Trademark Office*